United States Patent
Ryan

[11] Patent Number: 5,833,213
[45] Date of Patent: Nov. 10, 1998

[54] MULTIPLE DOSE DRUG VIAL ADAPTER FOR USE WITH A VIAL HAVING A PIERCEABLE SEPTUM AND A NEEDLELESS SYRINGE

[75] Inventor: Dana Wm. Ryan, Woodward, Okla.

[73] Assignee: Rymed Technologies, Inc., Woodward, Okla.

[21] Appl. No.: 906,661

[22] Filed: Aug. 7, 1997

Related U.S. Application Data

[63] Continuation-in-part of Ser. No. 581,057, Dec. 29, 1995, and a continuation-in-part of Ser. No. 841,281, Apr. 29, 1997.

[51] Int. Cl.⁶ .................................................. A61M 5/00
[52] U.S. Cl. ...................... 251/149.1; 604/249; 604/256; 604/905
[58] Field of Search ........................ 251/149.1; 604/256, 604/905, 249

[56] References Cited

U.S. PATENT DOCUMENTS

| | | |
|---|---|---|
| 3,192,949 | 7/1965 | De See . |
| 3,799,171 | 3/1974 | Patel . |
| 3,806,086 | 4/1974 | Cloyd . |
| 3,831,629 | 8/1974 | Mackal et al. . |
| 4,128,098 | 12/1978 | Bloom et al. . |
| 4,349,021 | 9/1982 | Raible . |
| 4,559,043 | 12/1985 | Whitehouse et al. . |
| 4,617,015 | 10/1986 | Foltz . |
| 4,681,132 | 7/1987 | Lardner . |
| 4,683,916 | 8/1987 | Raines . |
| 4,723,550 | 2/1988 | Bales et al. . |
| 4,776,369 | 10/1988 | Lardner et al. . |
| 4,908,018 | 3/1990 | Thomsen . |
| 4,915,687 | 4/1990 | Sivert . |
| 4,934,655 | 6/1990 | Blenkush et al. . |
| 5,024,657 | 6/1991 | Needham et al. . |
| 5,060,812 | 10/1991 | Ogle, II . |
| 5,085,645 | 2/1992 | Purdy et al. . |
| 5,108,380 | 4/1992 | Herlitze et al. . |
| 5,116,021 | 5/1992 | Faust et al. . |

(List continued on next page.)

*Primary Examiner*—Kevin Lee
*Attorney, Agent, or Firm*—David P. Gordon; David S. Jacobson; Thomas A. Gallagher

[57] ABSTRACT

A drug vial adapter according to the invention includes: a first coupling member having a female luer connector (preferably a luer lock) with a fluid path therethrough, a flange having a first sealing ring seat formed therein and a first mating structure; a second cylindrical coupling member having a centrally located septum piercing tube with a fluid path therethrough and a second mating structure; and a valve member including a valve stem and a resilient valve body having an annular sealing surface. A valve body seat is formed in the interior of the second coupling member by a plurality of radially arranged stepped vanes. According to a preferred embodiment, the second coupling member is formed as a stepped cylinder having a relatively large diameter adjacent the point of the septum piercing tube, a relatively small diameter adjacent the valve body seat and an intermediate diameter therebetween. The presently preferred valve body is substantially frustroconical having a relatively broad end with a stepped axial bore defining the annular sealing surface. The presently preferred valve stem has a stepped cylindrical portion which fits into the axial bore of the valve body and a pair of spaced apart upstanding members which extend into the female luer.

20 Claims, 8 Drawing Sheets

U.S. PATENT DOCUMENTS

| | | |
|---|---|---|
| 5,163,922 | 11/1992 | McElveen, Jr. . |
| 5,181,913 | 1/1993 | Erlich . |
| 5,181,921 | 1/1993 | Makita et al. . |
| 5,195,967 | 3/1993 | Nakao et al. . |
| 5,199,947 | 4/1993 | Lopez et al. . |
| 5,201,725 | 4/1993 | Kling . |
| 5,203,775 | 4/1993 | Frank et al. . |
| 5,215,538 | 6/1993 | Larkin . |
| 5,217,434 | 6/1993 | Arney . |
| 5,230,706 | 7/1993 | Duquette . |
| 5,242,393 | 9/1993 | Brimhall et al. . |
| 5,242,423 | 9/1993 | Goodsir et al. . |
| 5,242,432 | 9/1993 | DeFrank . |
| 5,250,028 | 10/1993 | Theeuwes et al. . |
| 5,250,034 | 10/1993 | Appling et al. . |
| 5,251,873 | 10/1993 | Atkinson et al. . |
| 5,259,839 | 11/1993 | Burns . |
| 5,269,771 | 12/1993 | Thomas et al. . |
| 5,280,876 | 1/1994 | Atkins . |
| 5,284,475 | 2/1994 | Mackal . |
| 5,289,849 | 3/1994 | Paradis . |
| 5,290,263 | 3/1994 | Wigness et al. . |
| 5,300,033 | 4/1994 | Miller . |
| 5,300,044 | 4/1994 | Classey et al. . |
| 5,308,334 | 5/1994 | Sancoff . |
| 5,322,518 | 6/1994 | Schneider et al. . |
| 5,330,435 | 7/1994 | Vaillancourt . |
| 5,334,170 | 8/1994 | Moroski . |
| 5,336,174 | 8/1994 | Daoud et al. . |
| 5,336,192 | 8/1994 | Palestrant . |
| 5,338,313 | 8/1994 | Mollenauer et al. . |
| 5,353,837 | 10/1994 | Faust . |
| 5,356,375 | 10/1994 | Higley . |
| 5,360,413 | 11/1994 | Leason et al. . |
| 5,364,371 | 11/1994 | Kamen . |
| 5,370,624 | 12/1994 | Edwards et al. . |
| 5,390,898 | 2/1995 | Smedley et al. . |
| 5,391,150 | 2/1995 | Richmond . |
| 5,395,348 | 3/1995 | Ryan . |
| 5,399,171 | 3/1995 | Bowman et al. . |
| 5,401,255 | 3/1995 | Sutherland et al. . |
| 5,405,323 | 4/1995 | Rogers et al. . |
| 5,425,465 | 6/1995 | Healy . |
| 5,429,256 | 7/1995 | Kestenbaum . |
| 5,433,330 | 7/1995 | Yatsko et al. . |
| 5,464,938 | 11/1995 | Werge et al. . |
| 5,533,983 | 7/1996 | Haining ............................ 251/149.1 X |
| 5,535,771 | 7/1996 | Purdy et al. . |
| 5,573,525 | 11/1996 | Watson et al. . |
| 5,578,059 | 11/1996 | Patzer . |

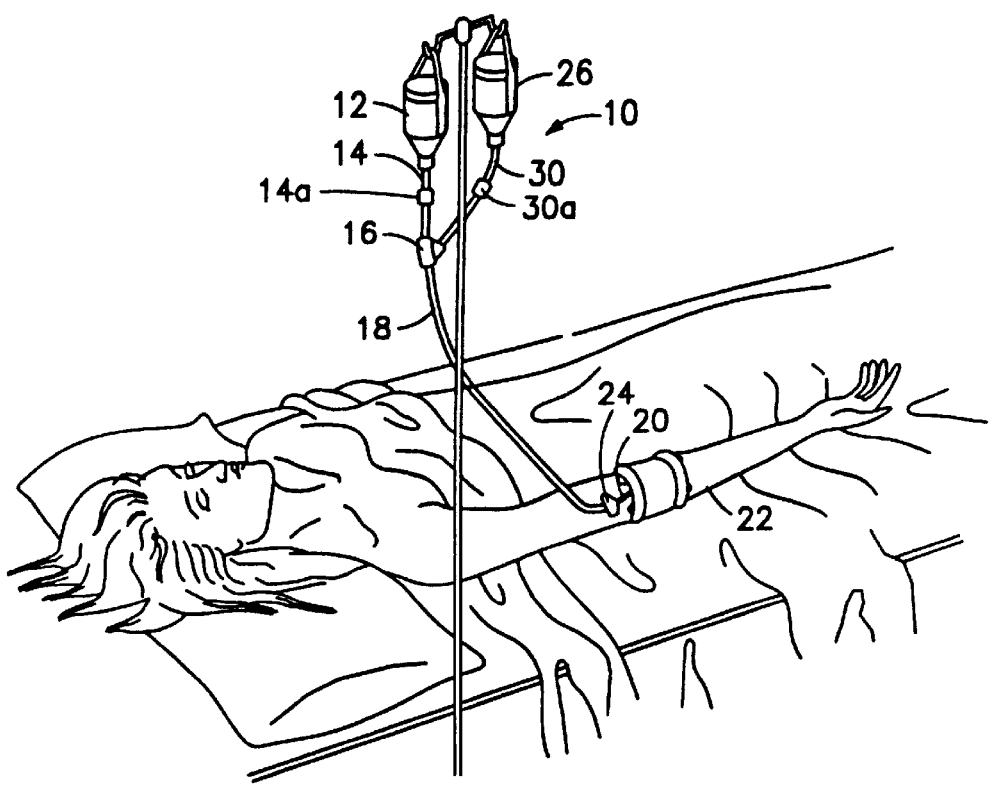
FIG.1
PRIOR ART
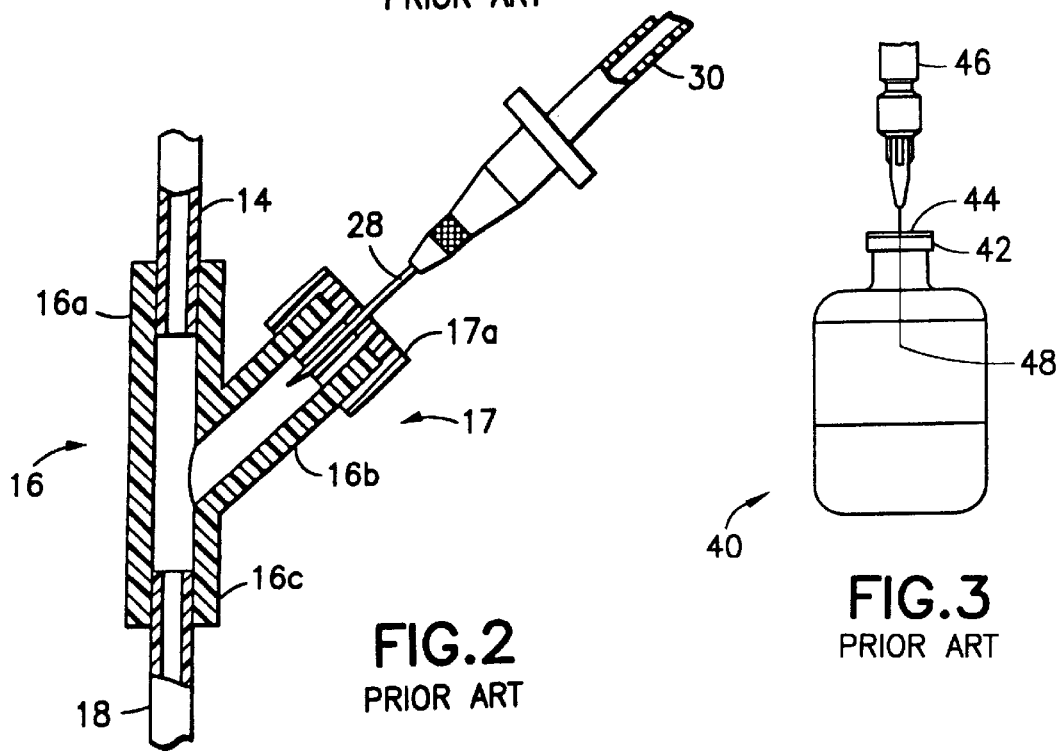
FIG.2
PRIOR ART
FIG.3
PRIOR ART

MULTIPLE DOSE DRUG VIAL ADAPTER FOR USE WITH A VIAL HAVING A PIERCEABLE SEPTUM AND A NEEDLELESS SYRINGE

This application is a continuation-in-part of my co-pending applications Ser. No. 08/581,057, filed Dec. 29, 1995, and Ser. No. 08/841,281, filed Apr. 29, 1997 the complete disclosures of which are hereby incorporated by reference herein.

BACKGROUND OF THE INVENTION

1. Field of the Invention

This invention relates to medical IV administration line connectors. More particularly, this invention relates to needleless injection ports for the safe infusion and/or aspiration of fluids in intravenous and blood administration therapy. Most particularly, the invention relates to a vial adaptor which allows a drug vial intended for use with a hypodermic needle to be used with a needleless injector.

2. State of the Art

Intravenous therapy has a long history of use in supplying patients with pharmaceuticals, liquid nourishment, or blood products. Prior art FIG. 1 shows that the current or conventional way of introducing parenteral liquid solutions and/or blood and blood products into a patient is by the conventional gravity feeding system 10. The feeding system 10 includes a container 12 that is either a bottle or bag for the parenteral solution, a tube 14 extending from the bottle or bag and connected to a Y-injection site 16 (piggyback or secondary Y-injection site), and a tube 18 from the Y-injection site 16 to a needle or catheter 20 which is inserted into a vein in the arm 22 of the patient. The vein-access needle or catheter is taped to the patient with adhesive tape 24 so that the chance of a detachment and disconnect from the vein is minimized.

Supplemental intravenous therapy from a piggyback or secondary bottle or bag 26 is introduced through the Y-injection site 16 into the primary intravenous administration set 10. As shown in prior art FIG. 2, the Y-injection site 16 which is integrated into the primary intravenous administration set 10 consists of two tubular conduits 16a, 16b which merge into a third tubular conduit 16c. The tubing 14 from the bottle or bag of parenteral solution of the primary intravenous administration set 10 is attached into the inlet port 16a of the Y-injection site. In similar fashion, the tube 18 is attached into the exit port 16c of the Y-injection site. A sealed entry port segment 17 of the Y-injection site 16 is provided by the extension conduit 16b which has a standard, self-sealing latex rubber septum 17a at its inlet port to seal this port from leakage. Consequently, it is difficult for pathogens to enter the Y-injection site 16 via the septum port 17 because of the seal 17a. This self-sealing septum 17a is of a conventional design and includes coaxial annular aprons which fit over the conduit wall and grip the external and internal wall surfaces to hold the septum securely to the conduit 16b. Typically, a plastic shrink-band (not shown) is shrunk on the outer wall of the septum 17a to securely connect it to the extension conduit 16b.

Referring now to prior art FIGS. 1 and 2 together, the supplemental intravenous solution is introduced into the primary intravenous administration set 10 through the Y-injection site 16 by way of a primed piggyback or secondary intravenous set 26. The piggyback or secondary intravenous set 26 has a hollow-bore needle 28 attached to its distal end, which in turn is inserted through the self-sealing septum 17a of the Y-injection site 16 and into the extension conduit 16b. This needle 28 is connected to a tube 30 which is connected to a drip-chamber (not shown) of the piggyback or secondary intravenous set 26. A roller clamp 14a, 30a is typically used on both the primary and piggyback/secondary intravenous sets to control liquid flow rates into the patient.

The Y-injection site may also be used for the introduction of pharmaceuticals or other medications which are available in small vials. Referring now to prior art FIG. 3, a pharmaceutical vial 40 containing a liquid medication is provided with a cap 42 having a septum 44. Medication is removed from the vial 40 with a hypodermic needle 46 by piercing the septum 44 with the sharp point 48 of the hypodermic needle 46. The vial 40 is typically inverted with the hypodermic needle so inserted and liquid medication is withdrawn from the vial with the hypodermic needle. The needle is then inserted through the septum 17a of the Y-site and the drug is pushed into the patient. Alternatively, the drug may be similarly injected through a heparin lock (not shown) having a similar septum, but which is located closer to the patient's arm.

My prior applications which have been previously incorporated herein by reference explain the many disadvantages of hollow needle fluid administration devices and disclose several different embodiments of needleless injection ports. In addition, the prior art generally recognizes the disadvantages of hypodermic needles and the fact that needleless syringes are widely available.

U.S. Pat. Nos. 5,060,812; 5,425,465; 5,433,330; and 5,573,525 each disclose a special type of medication container which can be used with a needleless syringe. However, none of these containers has gained popularity. Thus, injectable medication is still most often provided in a container which can only be accessed with a hypodermic needle.

U.S. Pat. No. 5,429,256 to Kestenbaum discloses an apparatus which snaps onto the top of a needle pierceable drug vial and allows a needleless syringe to withdraw fluid from the vial. The apparatus includes a female luer within which a ferrule with a sharp lance is disposed. When a male luer is connected to the female luer, the ferrule is displaced and the lance pierces the septum of the drug vial. After the fluid is withdrawn, there is no apparent way to reseal the pierced septum other than by removing the female luer from the apparatus, which is what Kestenbaum discloses. However, when the female luer is so removed, the sharp lance is exposed and the danger of needlesticks is again present.

SUMMARY OF THE INVENTION

It is therefore an object of the invention to provide an adapter for use with a medical vial having a septum cap which allows a needleless syringe to draw fluid from the vial.

It is also an object of the invention to provide a vial adapter which accommodates vials of different sizes.

It is a further object of the invention to provide a vial adapter which includes a luer activated valve.

It is an additional object of the invention to provide a vial adapter with a luer activated valve which tolerates variations in male luer dimensions with little affect on the flow rate.

In accordance with the objects stated above, a drug vial adapter according to the invention includes: a first coupling member having a female luer connector (preferably a luer lock) with a fluid path therethrough, and a flange having a first sealing ring seat formed therein and a first mating means; a second cylindrical coupling member having a centrally located septum piercing tube with a fluid path therethrough and a second mating means; and a valve member including a valve stem and a resilient valve body having an annular sealing surface. A valve body seat is formed in the interior of the second coupling member by a plurality of radially arranged stepped vanes. According to a preferred embodiment, the second coupling member is formed as a stepped cylinder having a relatively large diameter adjacent the point of the septum piercing tube, a relatively small diameter adjacent the valve body seat and an intermediate diameter therebetween. The presently preferred valve body is substantially frustroconical, tapering in diameter toward the point of the septum piercing tube, and having a relatively broad end with a stepped axial bore defining the annular sealing surface. The presently preferred valve stem has a stepped cylindrical portion which fits into the axial bore of the valve body and a pair of spaced apart upstanding members which extend into the female luer. The upstanding members preferably have curved outer surfaces and chamfered edges. A pair of inclined surfaces meet at a peak between the upstanding members and ramp outward toward the cylindrical portion of the valve stem.

The vial adapter is assembled by snapping the stepped cylindrical portion of the valve stem to the stepped bore of the valve body, placing the valve body in the valve body seat of the second coupling member, placing the first coupling member over the valve stem so that the stem enters the female luer and the mating means on the flange on the first coupling member mates with the mating means of the second coupling member. While applying axial pressure to join the coupling members, sonic energy is applied to weld the mating means and hence the members together. Under the influence of sonic energy, the mating means melt at their point of contact and move towards each other to form a strong fluid-tight fusion. As assembled in this fashion, the valve body is stabilized, centered, and biased towards the first sealing ring.

The vial adapter is attached to a drug vial by aligning the point of the septum piercing tube with the center of the septum of the vial and by pushing the tube through the septum. As the tube passes through the septum, the neck of the vial is received by the second cylindrical coupling member. The stepped diameter of the coupling member allows the adapter to be used with vials having necks of different diameter. According to preferred aspects of the invention, the interior of the neck receiving portion of the adapter is provided with means for frictionally engaging the neck of the vial. Preferably, the neck receiving portion of the adapter is made of a resilient material and/or is provided with expansion strain relief means so that the adapter will snugly grip the neck of the vial.

After the vial adapter is attached to a vial, it remains in place so that multiple doses of medication may be withdrawn from the vial. When a needleless syringe is attached to the vial adapter, the valve stem is moved towards the vial and the resilient valve body is compressed and moved away from the first sealing ring opening a fluid path from the septum piercing tube into the female luer, and thus into the needleless syringe. When the syringe is removed from the adapter, the resilient valve body expands and seals the fluid path.

Additional objects and advantages of the invention will become apparent to those skilled in the art upon reference to the detailed description in conjunction with the accompanying drawings.

BRIEF DESCRIPTION OF THE DRAWINGS

FIG. 1 is a schematic view of a prior art intravenous administration set coupled to a patient;

FIG. 2 is a broken side elevation view, in partial section, of a prior art Y-injection site;

FIG. 3 is a broken, partially transparent side elevation view of a prior art drug vial with a hypodermic needle inserted through the septum cap;

DETAILED DESCRIPTION OF THE PREFERRED EMBODIMENTS

Figure 4:
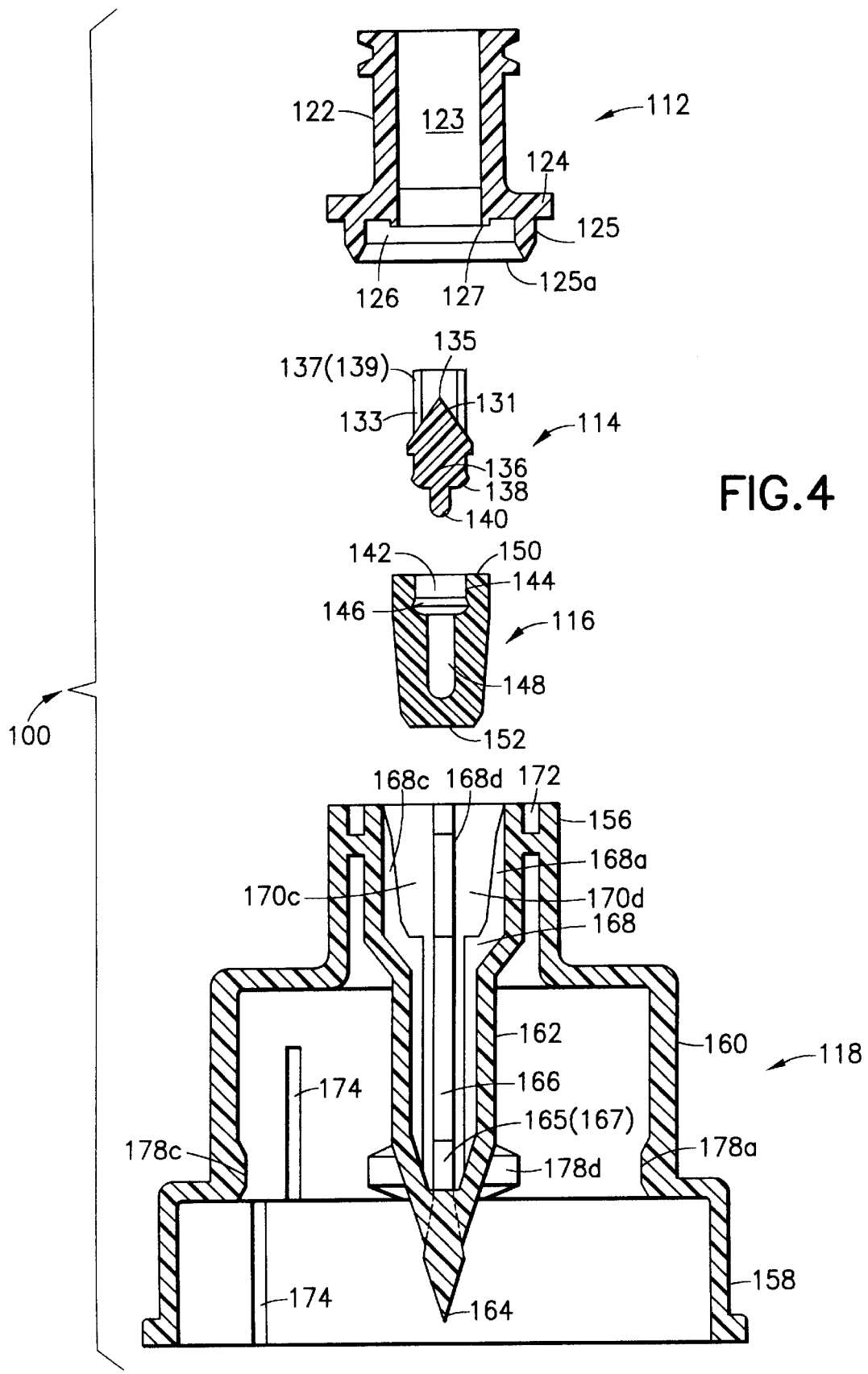
FIG. 4 is an enlarged exploded sectional view of the components of a vial adapter according to the invention.

Turning now to FIG. 4, a vial adapter 100 according to the invention generally includes: a first coupling member 112, a valve stem 114, a resilient valve body 116, and a second coupling member 118. The first coupling member 112 is a female luer connector (preferably a luer lock) 122 having a flange 124 from which extends a cylindrical mating means 125 with a tapered edge 125a. The female luer connector 122 provides a fluid path 123 to the interior 126 of the cylindrical mating means 125. At the opening from the female luer into the interior 126, a first sealing ring seat 127 is formed.

Figure 4A:
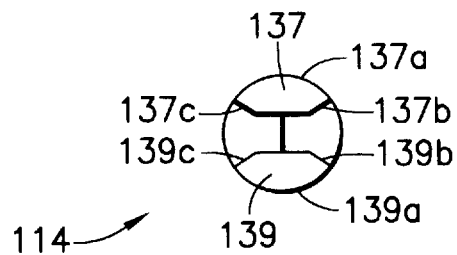
FIG. 4a is a top view of the valve stem component of the vial adapter.

The valve stem 114 has a cylindrical portion 136 with a circumferential flange 138, and an axial stabilizing pin 140 at one end and a pair of spaced apart upstanding members 137, 139 at the other end. As seen in FIG. 4a, the upstanding members preferably have curved outer surfaces 137a, 139a and chamfered edges 137b, 137c, 139b, 139c. As seen in FIG. 4, a pair of inclined surfaces 131, 133 meet at a central peak 135 between the upstanding members and ramp downward and outward toward the cylindrical portion 136 of the valve stem 114. According to a presently preferred embodiment, the angle defined by the central peak 135 is approximately 69°. This valve stem design according to the invention can be made easily and inexpensively by injection molding.

Figure 7:
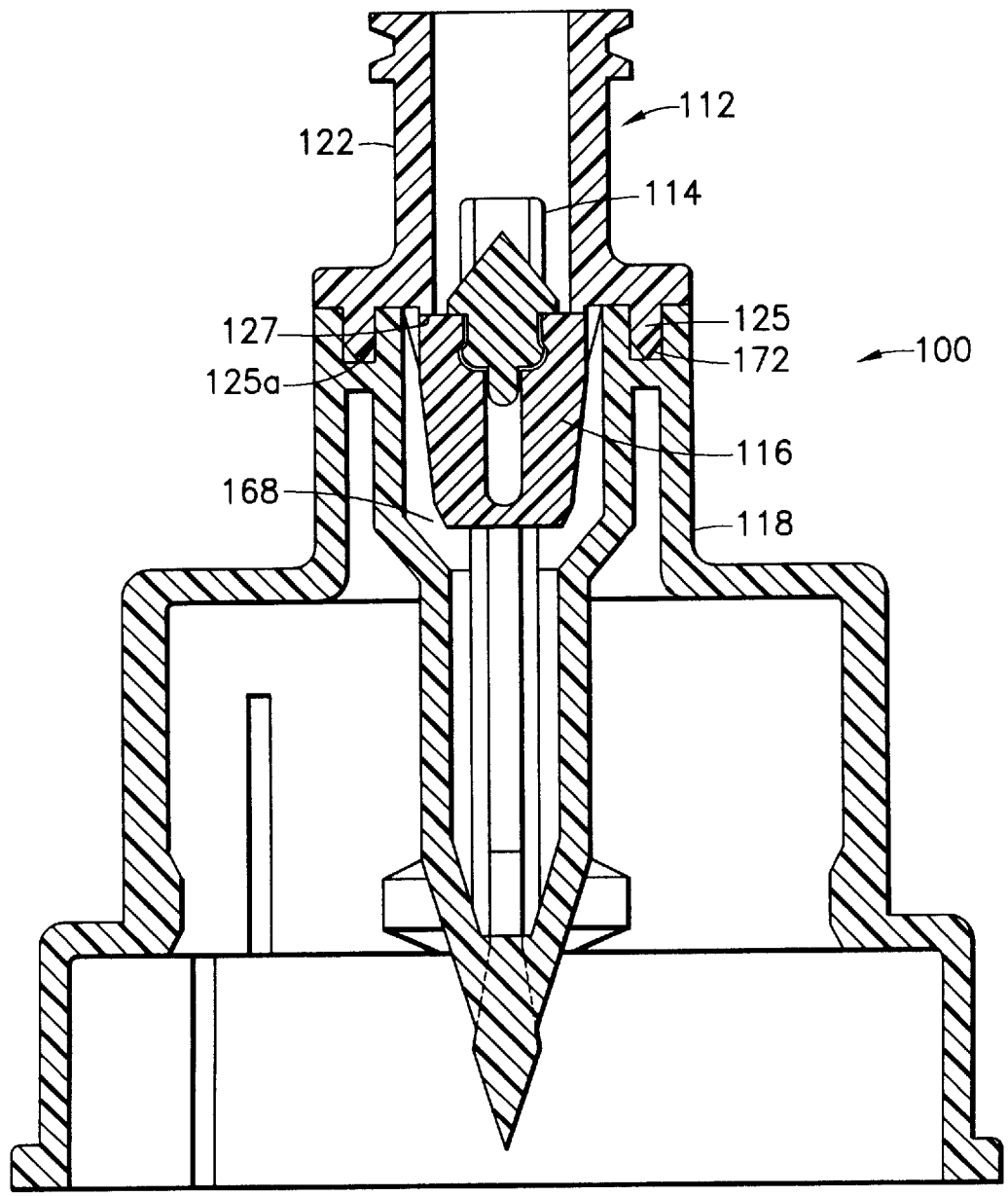
FIG. 7 is an enlarged sectional view of the assembled vial adapter.
Figure 8:
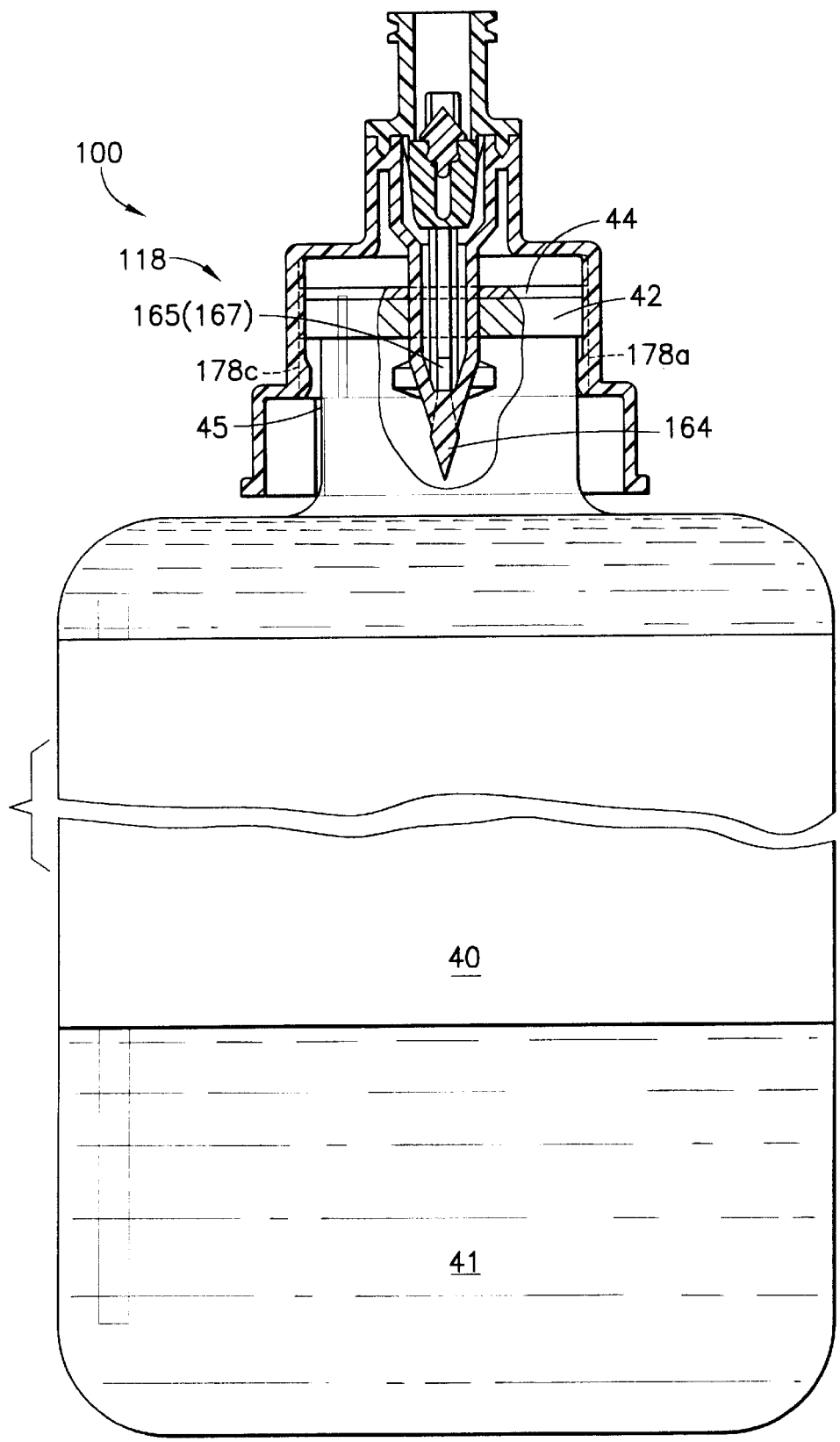
FIG. 8 is an enlarged, partially transparent, partially sectional view of the vial adapter attached to a drug vial.
Figure 9:
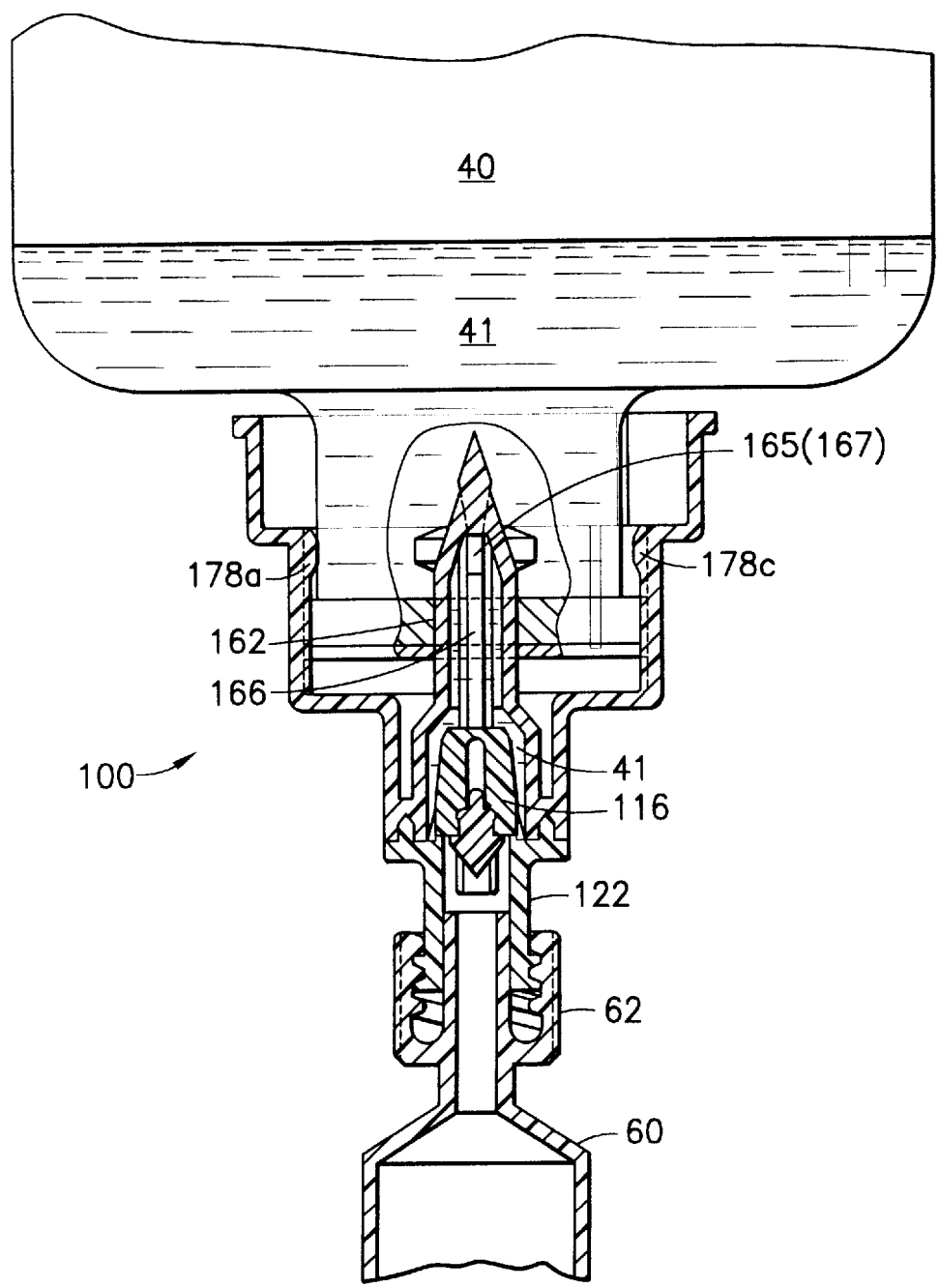
FIG. 9 is an enlarged, broken, partially transparent, partially sectional view of the vial adapter attached to a drug vial with a luer coupling syringe in an early stage of attachment to the first coupling component of the vial adapter.

The resilient valve body 116 is substantially frustroconical with an outer surface which is substantially free of concavities, a broader end serving as an annular sealing surface 150 and with a narrower end 152. The annular surface 150 is defined by an axial bore 142. The axial bore 142 has a relatively large diameter portion 144 with an interior surface groove 146 and a relatively small diameter portion 148. The valve stem 114 and the valve body 116 snap together as shown in FIGS. 7–9. More specifically, the portion 144 of the bore 142 in the valve body 116 receives the cylindrical portion 136 of the valve stem 114. The circumferential flange 138 has a diameter slightly larger than the diameter of the portion 144 of the bore 142. When the stem 114 is inserted into the body 116, the flange 138 stretches the resilient body 116 until the flange reaches the groove 146 in the bore 142. The groove 142 has a diameter just slightly smaller than the diameter of the flange 138. The pieces snap together when the flange 138 embraces the groove 146, forcing the groove 146 to expand. This inhibits the pieces from separating. The axial stabilizing pin 140 of the valve stem 114 is received by the small diameter portion 148 of the bore 142. It should be noted that length of the pin 140 is shorter than the length of the small diameter portion 148 of the bore 142. Thus, when the stem is pushed into and compresses the valve body 116, the valve body 116 can expand into the portion 148 of the bore 142.

Figure 4B:
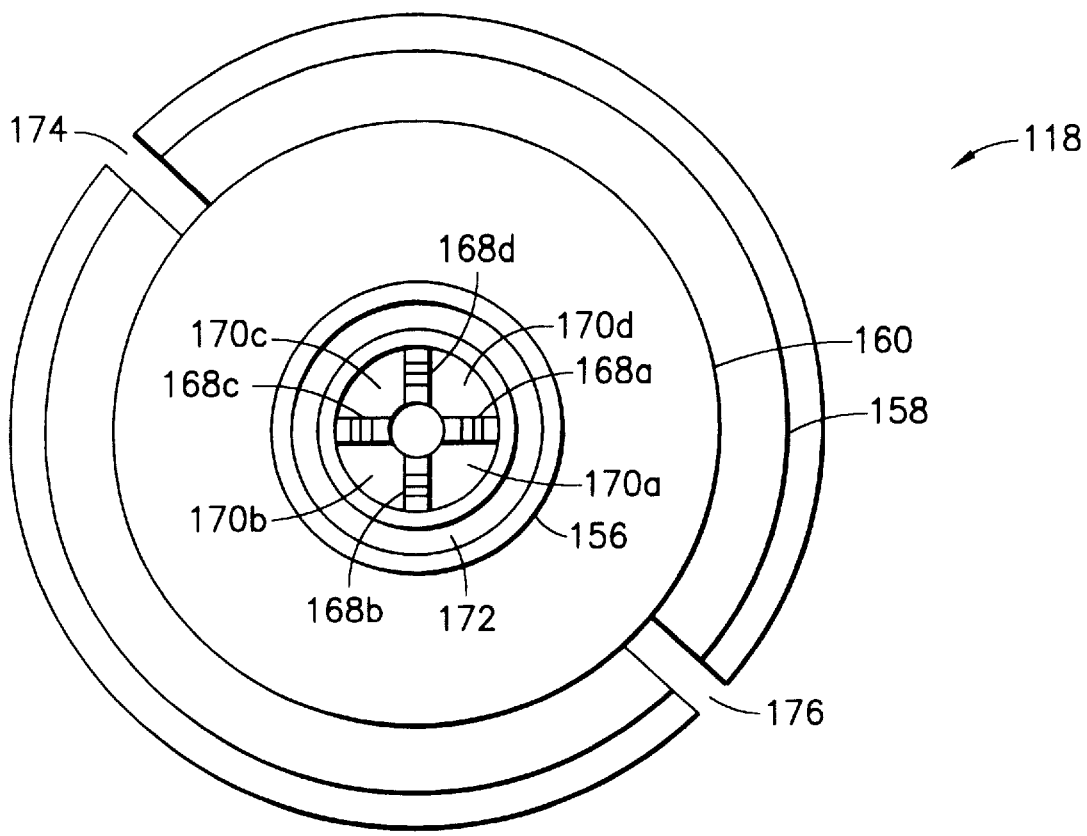
FIG. 4b is a top view of the second coupling component of the vial adapter.
Figure 5:
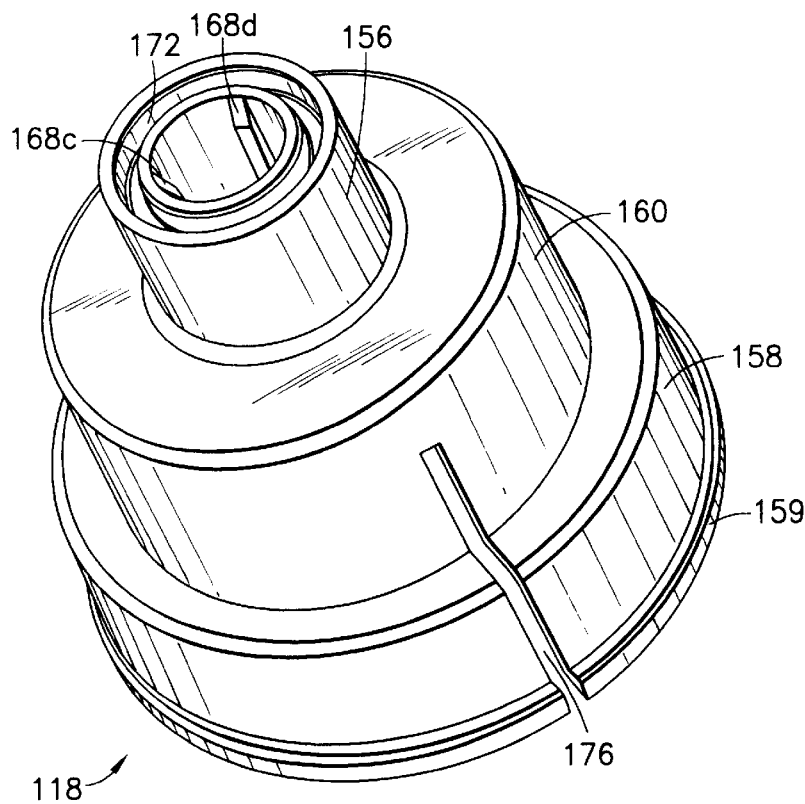
FIG. 5 is an enlarged perspective top view of the second coupling component of the vial adapter.
Figure 6:
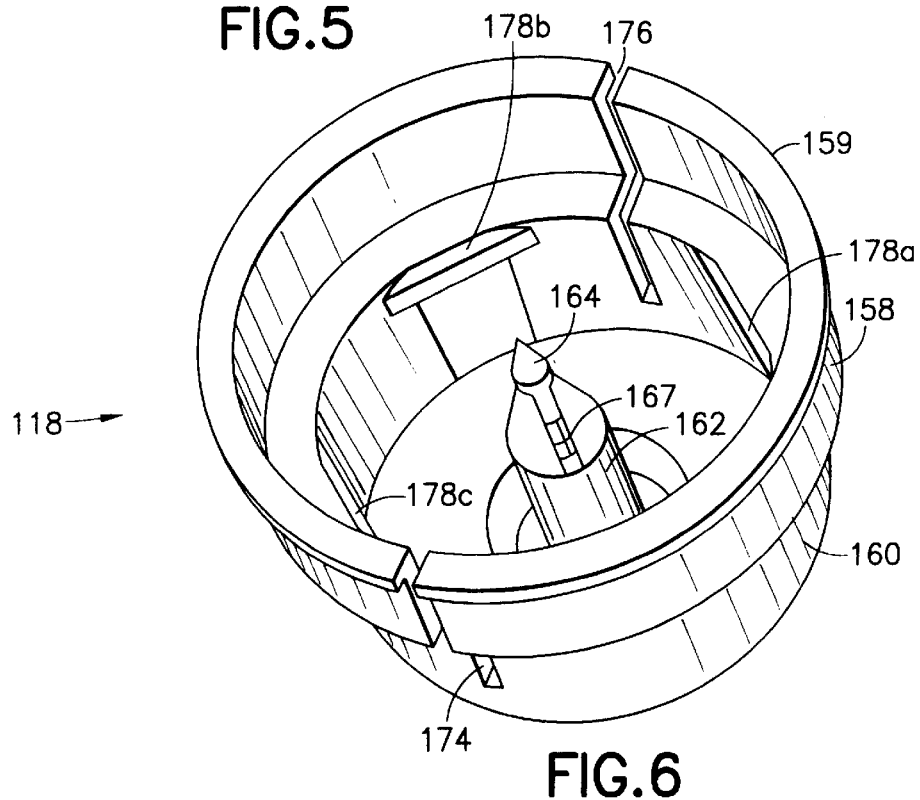
FIG. 6 is an enlarged perspective bottom view of the second coupling component of the vial adapter.

The second coupling member 118 is a stepped cylindrical member having a relatively small diameter portion 156, a relatively large diameter portion 158, and an intermediate diameter portion 160 therebetween. The coupling member 118 has a centrally located tube 162 with a sharp point 164. The tube 162 has an interior fluid path 166. At one end, the fluid path terminates in a valve body seat 168 inside the interior of the small diameter portion 158. At the other end, the fluid path terminates with lateral openings 165, 167 (FIG. 6) adjacent the point 164. The valve body seat 168 includes a plurality of substantially stepped vanes 168a–168d (FIG. 4b). These vanes serve the function of consistently centering the valve in the seat after activation, such that no leakage is experienced even after numerous (e.g., one hundred) activations. In addition, spaces 170a–170d between the vanes provide a flow path for fluid around the valve body as described below. An annular channel mating means 172 is provided at the end of the cylinder 156 and is dimensioned to receive the cylindrical mating means 125 of the first coupling member 112.

As seen best in FIGS. 4, 4b, 5, and 6, the coupling member 118 is preferably provided with a pair of strain relieving slits 174, 176 which extend longitudinally along portions of the large diameter part and the intermediate diameter part of the second coupling member 118. Four radially inward projections 178a–178d are preferably provided on portions of the interior of the intermediate diameter portion 160. The projections 178a–178d are designed to frictionally engage the neck of a drug vial as described below with reference to FIG. 8 and the slits 174, 176 are designed to allow the coupling member 118 to expand slightly when the projections engage the neck of the vial. As shown in the Figures, the coupling member is also provided with a flange 159 at the end of the large diameter portion 158 which provides added strength to the coupling member.

Referring now to FIGS. 4 and 7, the vial adapter 100 is assembled by inserting the stem 114 into the valve body 116 as described above, placing the body 116 of the valve member in the valve body seat 168 of the second coupling member 118, and placing the first coupling member 112 over the valve stem 114 so that the stem enters the female luer 122 and the tapered edge 125a of the cylindrical mating means 125 rests inside the annular channel 172 of the second coupling member 118. While applying axial pressure to the first and second coupling members, the mating means and the first and second coupling members are welded by the application of sonic energy. Indeed, under the influence of sonic energy, the cylindrical members melt at their point of contact and move towards each other to form a string fluid-tight fusion. As assembled in this fashion, the valve body 116 is stabilized, centered, and biased towards the first sealing ring 127.

Turning now to FIG. 8, the vial adapter 100 according to the invention is attached to a conventional medical drug vial 40 by aligning the point 164 of the septum piercing tube 162 with the center of the septum 44 of the vial and by pushing the tube through the septum. As the tube passes through the septum, the neck 45 of the vial is received by the second cylindrical coupling member 118 and is frictionally engaged by the projections 178a–178d. When so attached, the lateral fluid port openings 165, 167 reside inside the vial 40 providing access to the contents of the vial via the luer 122.

Figure 10:
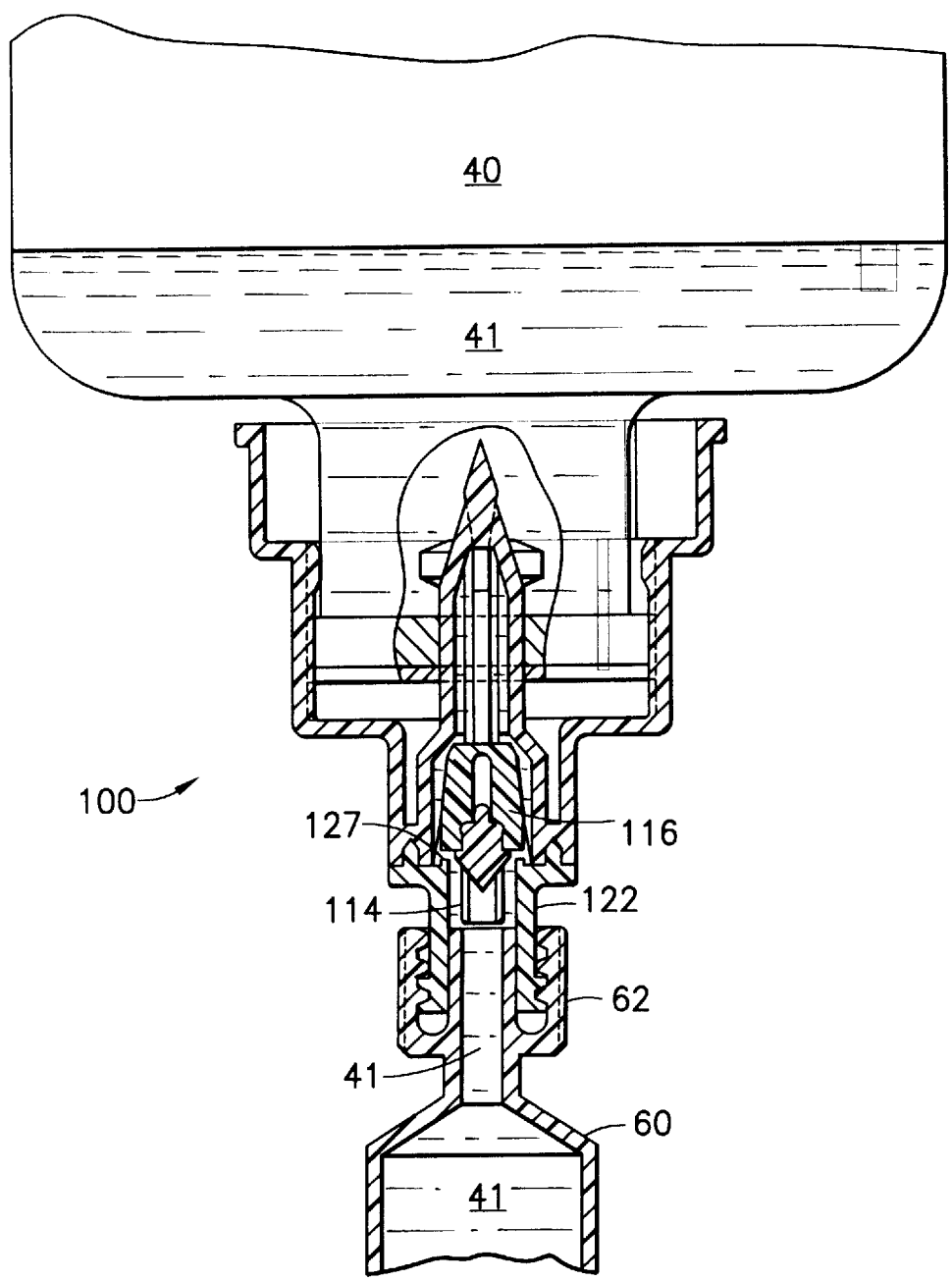
FIG. 10 is a view similar to FIG. 9 with a luer coupling syringe fully attached to the first coupling component of the vial adapter.

As shown in FIGS. 9 and 10, after the vial adapter 100 is attached to the vial 40, the contents 41 of the vial will flow through the lateral openings 165, 167 of the tube 162 and through the fluid path 166 when the vial is inverted. However, resilient valve body 116 prevents the contents 41 from flowing into the luer 122. When a conventional needle-less syringe 60 is attached to the luer 122, the male luer 62 of the syringe engages the valve stem 114 and compresses the resilient valve body 116 moving it away from the sealing ring seat 127 as shown in FIG. 10. The fluid contents 41 of the vial 40 flow freely now into the female luer 122 and into the male luer 62 of the syringe 60. Removing the syringe 60 from the luer 122 allows the valve body 116 to reseat as shown in FIG. 9.

The vial adapter according to the invention is designed to remain attached to the drug vial so that multiple doses may be withdrawn from the vial. When the contents of the vial are depleted, the vial may be disposed of with the adapter still attached. The vial adapter permits a needleless syringe to be used together with a conventional drug vial so that medication may be injected through a needleless injection port such as the injection ports disclosed in my earlier applications which were previously incorporated herein by reference.

There have been described and illustrated herein a multiple dose vial adapter for use with a drug vial having a pierceable septum and a needleless syringe. While particular embodiments of the invention have been described, it is not intended that the invention be limited thereto, as it is intended that the invention be as broad in scope as the art will allow and that the specification be read likewise. Thus, while a particular valve body and valve stem have been disclosed, it will be appreciated that other the valve bodies and valve stems disclosed in my previously incorporated co-pending applications could be utilized. Also, while particular configurations have been shown with regard to engaging protrusions and strain reliefs, it will be recognized that other types of protrusions and strain reliefs could be used with similar results obtained. Moreover, while particular configurations have been disclosed in reference to the shape of the septum piercing tube, it will be appreciated that other configurations could be used as well. Furthermore, while the valve body seat has been disclosed as having four stepped vanes, it will be understood that a different number of vanes can achieve the same or similar function as disclosed herein. It will therefore be appreciated by those skilled in the art that yet other modifications could be made to the provided invention without deviating from its spirit and scope as so claimed.

I claim:

1. A vial adapter for use with a vial having a pierceable septum, said vial adapter comprising:
   a) a first coupling member having a female luer at a first end of said first coupling member, and a first mating structure;
   b) a valve member having a stem and a resilient body with a sealing surface, said valve member disposed relative to said first coupling member with said stem extending into said female luer; and
   c) a second coupling member having a first open generally cylindrical chamber with a valve member support, a septum piercing member in fluid communication with said first cylindrical chamber, and a second mating structure for mating and coupling with said first mating structure, said second coupling member being coupled to said first coupling member with said valve member support supporting said resilient body of said valve member such that said sealing surface is biased against said female luer thereby blocking fluid communication between said female luer and said first cylindrical chamber.

2. An adapter according to claim 1, wherein:
said female luer and said stem extending into said female luer are sized such that,
upon coupling a needleless syringe to said female luer, the needleless syringe engages said stem and moves said stem toward said second coupling member, thereby compressing said resilient body, moving said sealing surface away from said female luer, and opening fluid communication between said female luer and said first cylindrical chamber, and
upon uncoupling the needleless syringe from said female luer, the needleless syringe disengages said stem and said resilient body expands towards said female luer such that said sealing surface contacts said female luer and blocks fluid communication between said female luer and said first cylindrical chamber.

3. An adapter according to claim 1, wherein:
said stem includes upstanding members each having a curved surface and a chamfered edge.

4. An adapter according to claim 1, wherein:
said stem and said resilient body are separate mating pieces, and
said stem is relatively rigid compared to said resilient body.

5. An adapter according to claim 4, wherein:
said stem is formed from a substantially rigid material.

6. An adapter according to claim 1, wherein:
said valve member support includes a fluid passage in fluid communication with said septum piercing member.

7. An adapter according to claim 6, wherein:
said valve member support comprises a plurality of radial vanes and said fluid passage comprises a space between said radial vanes.

8. An adapter according to claim 7, wherein:
said radial vanes have steps and said resilient body is supported by said steps.

9. An adapter according to claim 1, wherein:
one of said first mating structure and said second mating structure includes an annular channel; and
the other of said first mating structure and said second mating structure includes a cylinder dimensioned to fit inside said annular channel.

10. An adapter according to claim 9, wherein:
said first mating structure and said second mating structure are sonically welded.

11. An adapter according to claim 1, wherein:
said valve member support includes a plurality of vanes extending substantially the entire length of said first open generally cylindrical chamber.

12. An adapter according to claim 1, wherein:
said second coupling member has a second open generally cylindrical chamber within which said septum piercing tube is disposed.

13. An adapter according to claim 12, wherein:
said second cylindrical chamber is dimensioned to receive a neck of the vial.

14. An adapter according to claim 13, wherein:
said second cylindrical chamber has means for frictionally engaging the neck of the vial.

15. An adapter according to claim 14, wherein:
said second cylindrical chamber has means for expanding when frictionally engaging the neck of the vial.

16. A drug vial adapter for use with a vial having a pierceable septum, said vial adapter comprising:
   a) a septum piercing tube having a fluid path therethrough;
   b) a valve chamber in fluid communication with said fluid path;
   c) a first coupling structure for coupling to a needleless syringe; and
   d) a syringe activated valve in said valve chamber, said valve having a valve body and a valve stem, said stem extending into said first coupling structure, said valve body presenting a surface which is substantially free of concavities.

17. An adapter according to claim 16, wherein:
said valve body is substantially frustroconical.

18. An adapter according to claim 16, wherein:
said valve stem has a pair of inclined surfaces which meet at a peak and ramp outward toward said valve body.

19. An adapter according to claim 16, wherein:
said valve stem has a pair of upstanding spaced apart curved members.

20. An adapter according to claim 16, wherein:
said valve body is substantially frustroconical tapering in diameter toward said septum piercing tube and having a relatively broad end with a stepped axial bore defining an annular sealing surface, and
said valve stem has a stepped cylindrical portion which fits into said axial bore of said valve body.

* * * * *